US00PP20276P2

(12) United States Plant Patent
Hanes

(10) Patent No.: US PP20,276 P2
(45) Date of Patent: Sep. 8, 2009

(54) ***PELARGONIUM* PLANT NAMED 'AMRI WHIT09'**

(50) Latin Name: *Pelargonium hortorum (L.) L' Herit. ex Ait*
Varietal Denomination: Amri Whit09

(75) Inventor: Mitchell Hanes, Morgan Hill, CA (US)

(73) Assignee: Goldsmith Seeds, Inc., Gilroy, CA (US)

( * ) Notice: Subject to any disclaimer, the term of this patent is extended or adjusted under 35 U.S.C. 154(b) by 0 days.

(21) Appl. No.: 12/220,486

(22) Filed: Jul. 24, 2008

(51) Int. Cl.
*A01H 5/00* (2006.01)

(52) U.S. Cl. ..... Plt./326

(58) Field of Classification Search ..... Plt./325, Plt./326
See application file for complete search history.

*Primary Examiner*—Susan B McCormick Ewoldt
(74) *Attorney, Agent, or Firm*—S. Matthew Edwards

(57) ABSTRACT

A new *Pelargonium* plant named 'Amri Whit09,' particularly distinguished by the clean white flower color, light to medium green foliage, round and semi-compact habit, with good branching and garden performance.

1 Drawing Sheet

Latin name of the genus and species of the plant claimed: *Pelargonium hortorum* (*L.*) *L'Herit. ex Ait.*

Varietal denomination: 'Amri Whit09'.

BACKGROUND OF THE NEW PLANT

The present invention comprises a new *Pelargonium,* botanically known as *Pelargonium hortorum,* and hereinafter referred to by the variety name 'Amri Whit09'.

'Amri Whit09' is a product of a planned breeding program. The new cultivar 'Amri Whit09' has a clean white flower color, light to medium green foliage, round and semi-compact habit, with good branching and garden performance.

'Amri Whit09' originated from a sibling cross in a controlled breeding program in Gilroy, Calif. USA. The female parent was an unpatented hybrid seedling identified as '9912-3' with white flower color. '9912-3' has smaller flowers and is less vigorous than 'Amri Whit09'.

The male parent of 'Amri Whit09' was an unpatented hybrid seedling identified as '9912-2' with white color. '9912-2' has fewer petals, less vigor, and is earlier to flower than 'Amri Whit09'.

'Amri Whit09' was selected as one flowering plant within the progeny of the stated cross in 2005 in a controlled environment in Gilroy, Calif. USA.

The first act of asexual reproduction of 'Amri Whit09' was accomplished when vegetative cuttings were taken from the initial selection in the November 2005 in a controlled environment in Gilroy, Calif. USA.

Horticultural examination of plants grown from cuttings of the plant initiated in November 2005 in Gilroy, Calif., USA and continuing thereafter, has demonstrated that the combination of characteristics as herein disclosed for 'Amri Whit09' are firmly fixed and are retained through successive generations of asexual reproduction.

'Amri Whit09' has not been observed under all possible environmental conditions. The phenotype may vary significantly with variations in environment such as temperature, light intensity, and day length.

Plant Breeder's Rights for this cultivar were applied for in Canada on Dec. 24, 2007 and in Germany on Jul. 2, 2007. 'Amri Whit09' has not been made publicly available more than one year prior to the filing of this application.

DESCRIPTION OF THE DRAWING

The accompanying photographic drawing shows typical flower and foliage characteristics of 'Amri Whit09' with colors being as true as possible with an illustration of this type.

The photographic drawing shows a container of three flowering potted plants of the new variety, and a close-up of the flowers.

DETAILED BOTANICAL DESCRIPTION

The measurements were taken in Gilroy, Calif. USA, in August 2007 on plants that were growing in 14 inch containers containing 3 plants each. Cultures of these plants started in the greenhouse in April 2007 and were transferred to the outdoor containers in early June 2007. The plants were approximately 4 months old.

Color chart used: The Royal Horticultural Society Colour Chart (R.H.S.) 2001

BRIEF SUMMARY OF INVENTION

The following observations, measurements, and comparisons describe plants grown outside in Gilroy, Calif., USA. The following traits have been repeatedly observed and are determined to be basic characteristics of the new variety. The combination of these characteristics distinguishes this *Pelargonium* as a new and distinct variety.

TABLE 1

DIFFERENCES BETWEEN THE NEW VARIETY AND A SIMILAR VARIETY

| | 'Amri Whit09' | 'Fisroweiss' (U.S. Plant Pat. No. 16,974) |
|---|---|---|
| Vigor | More vigorous | Less vigorous |
| Peduncle length | Shorter | Longer |
| Foliage color | Lighter green | Darker green |
| Bud length | Longer | Shorter |

Plant:

*Form, growth and habit.*—Upright and rounded growth habit. Well-branched.

*Plant height.*—12–15 cm.
*Plant height* (*inflorescence included*).—22–24 cm.
*Plant width.*—13–16 cm.

Foliage:
*Arrangement.*—Alternate, simple.
*Immature, leaf color, upper surface.*—Between RHS 144A and B. Lower surface: RHS 144B.
*Mature, leaf color, upper surface.*—Closest to RHS 146A but more green. Lower surface: Closest to RHS 146B.
*Length.*—5.3–5.8 cm.
*Width.*—6.8–7.1 cm.
*Shape.*—Orbicular.
*Base shape.*—Reniform.
*Apex shape.*—Rounded.
*Margin.*—Slightly lobed; irregularly crenate.
*Texture.*—Hirsute, glandular hairs.
*Color of zone.*—No zone.
*Color of veins, upper surface.*—Indistinct.
*Color of veins, lower surface.*—RHS 146B.
*Petioles color.*—RHS 146B.
*Petioles length.*—2.6–2.9 cm.
*Diameter of petiole.*—0.2 cm.
*Texture.*—Hirsute.

Stem:
*Color of stem.*—RHS 146B.
*Length of stem.*—8–10 cm.
*Diameter.*—0.6–0.8 cm.
*Length of internodes.*—0.7–1.0 cm.
*Texture.*—Hirsute.

Inflorescence:
*Type.*—An umbel composed of 15–30 flowers and buds.
*Umbel diameter.*—6.5–8.0 cm.
*Umbel depth.*—5.5–6.5 cm.
*Color of peduncle.*—RHS 144A-B.
*Length of peduncle.*—8.6–10.5 cm.
*Peduncle diameter.*—0.3–0.4 cm.
*Texture.*—Short hirsute; glandular hairs.
*Pedicel color.*—RHS 146B.
*Length of pedicel.*—3.5–3.8 cm.
*Diameter of pedical.*—0.2.
*Texture.*—Glandular hairs.

Corolla:
*Form.*—Polypetalous, overlapping.
*Number of petals.*—5.
*Width of flower.*—4.2–4.5 cm.
*Color upper and lower petals, upper surface.*—RHS N155B but whiter.
*Color upper and lower petals, lower surface.*—RHS N155B but whiter.
*Length of upper petals.*—2.5 cm.
*Width of upper petals.*—2.0 cm.
*Petal shape.*—Obovate.
*Apex shape.*—Rounded.
*Margin.*—Entire.
*Petal texture.*—Papillose, both sides.
*Number of petaloids.*—Sometimes 2–3 smaller in various sizes.
*Color of petaloids.*—RHS N155B but whiter.
*Duration of flowering.*—Continuous flowering throughout the Summer.

Bud (when sepals first divide):
*Color.*—RHS N155B but whiter.
*Length.*—0.7–0.8 cm.
*Width.*—1.8–2.3 cm.
*Shape.*—Oblong to elliptic.
*Number of sepals.*—5, fused at the base.
*Color of sepals.*—RHS 144B.
*Length of sepals.*—1.3–1.4 cm.
*Width of sepals.*—0.5–0.6 cm.
*Sepal shape.*—Lanceolate.
*Apex shape.*—Acute.
*Margins.*—Entire.
*Texture.*—Long hirsute/villous; glandular hairs.

Reproductive organs:
*Pistil.*—1.
*Length.*—1.0–1.1 cm.
*Style color.*—RHS N155B but whiter.
*Style length.*—0.2–0.3 cm.
*Stigma color.*—RHS N155B but whiter.
*Number of anthers.*—About 5.
*Length filaments.*—0.5–0.7 cm.
*Color of filaments.*—RHS N155B but whiter.
*Pollen amount.*—Moderate.
*Color of pollen.*—RHS N25A.
*Fertility/seed set.*—Not observed on this hybrid.

Disease/pest resistance: Disease resistance and/or susceptibility has not been observed on this hybrid.

What is claimed is:

1. A new and distinct variety of *Pelargonium* plant named 'Amri Whit09', substantially as illustrated and described herein.

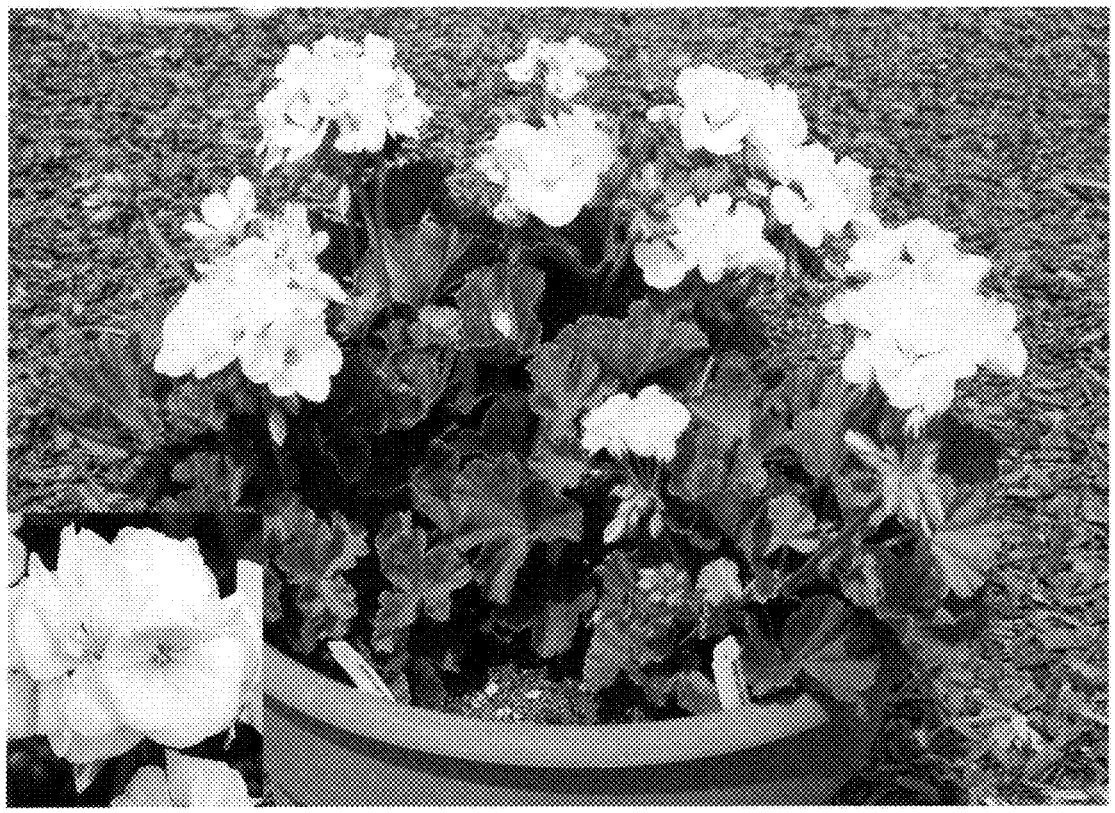

* * * * *